| [19] | [11] | Patent Number: | 4,965,335 |
| --- | --- | --- | --- |

United States Patent
Smith

[45] Date of Patent: Oct. 23, 1990

[54] HIGH-TEMPERATURE EXPANDING ORGANO-PHOSPHORUS MONOMER/POLYMERS

[75] Inventor: James D. B. Smith, Monroeville, Pa.

[73] Assignee: Westinghouse Electric Corp., Pittsburgh, Pa.

[21] Appl. No.: 325,749

[22] Filed: Mar. 20, 1989

[51] Int. Cl.$^5$ .................. C08G 59/40; C08G 79/04
[52] U.S. Cl. .................. 528/108; 528/398; 558/117; 558/155
[58] Field of Search .............. 528/108, 398; 558/117, 558/155

[56] References Cited

U.S. PATENT DOCUMENTS

| 4,082,897 | 4/1978 | Hechenbleikner | 528/398 X |
| 4,087,403 | 5/1978 | Moedritzer | 528/398 X |
| 4,254,351 | 3/1981 | Smith | 310/45 |
| 4,316,006 | 2/1982 | McEwen | 528/108 X |
| 4,387,215 | 6/1983 | Bailey | 528/354 |
| 4,812,502 | 3/1989 | Cipriani et al. | 558/155 X |

OTHER PUBLICATIONS

Kobayashi, et al., "Cationic Ring-Opening Polymerization of 2-Phenyl-1,3,2-dioxaphosphepane, a Seven-Membered Cyclic Phosphonite," 19 Macromolecules 466–469 (1986).

*Primary Examiner*—Earl Nielsen

[57] ABSTRACT

A method of producing organo-phophorus polymers is disclosed. The polymers will exhibit zero shrinkage and even expansion, will be useful in high voltage, high temperature electrical applications and will exhibit mechanical strength and flame retardant properties.

16 Claims, No Drawings

HIGH-TEMPERATURE EXPANDING ORGANO-PHOSPHORUS MONOMER/POLYMERS

FIELD OF THE INVENTION

The present invention relates to high temperature organo-phosphorus polymers and the monomers and methods of preparing high temperature organo-phosphorus polymers.

BACKGROUND OF THE INVENTION

Since the discovery of simple polymers many years ago, polymers of all kinds have emerged for a variety of uses, including manufacture of textiles, paints, plastics, synthetic rubbers, insulation, adhesives to name only a few. Polymers exist in two primary forms, thermoplastic polymers, which may be recurred, and thermosetting polymers, such as polystyrene, epoxies, etc., which cannot be recurred.

A common phenomenon occurring as a monomer is polymerized involves volumetric shrinkage of up to 15% based on the resulting polymer formed. This shrinkage represents an undesirable feature of polymers, as there exist many applications in which 0% shrinkage or "zero shrinkage," and even volume expansion upon polymerization are desirable.

Several "oxa-spiro" monomers have been identified that expand during polymerization. See, e.g., W. J. Bailey, et al.: J. Polym. Sci., Polym. Lett. Ed., 18: 771-773 (1980); J. Polym. Sci., Polym. Symp., 64: 17-26 (1978); J. Rubber Res., Inst. Sci. Lanko., 54: 566-75 (1977); J. Polym. Sci., Polym. Symp., 56: 117-27 (1976); J. Polym. Sci., Polym. Chem. Ed., 14: 1735-41 (1976); Makromol. Chem., 177, No. 11: 3231-5(1976); Polym. Prepr., ACS Polym. Chem. Div., 15:445-50 (1974); J. Macromol Sci., Chem. Publ., A9, No. 5: 849-65 (1975); J. Polym. Sci., Polym. Chem. Ed., 13: 2525-30 (1975); Makromol. Chem., 176: 2897-903 (1975); J. Poly. Sci., Polym. Lett. Ed., 13: 193-5 (1975); Polym. Prepr., ACS Polym. Chem. Div., 14: 1169-74 (1973); Polym. Prepr., ACS Polym. Chem. Div., 13: 281-6 (1972); W. J. Bailey and T. Endo, J. Polym. Sci., Polym. Lett. Ed., 18: 25-27 (1980); and W. J. Bailey, R. L. Sun, H. K. Endo, H. Iwana, R. Teushima, K. Saigou, and M. M. Bitritto, ACS Symp. Ser., Ring-Opening Polym., Int. Symp., 59: 38-59 (1977). Typical of these bicyclic oxa-spiro monomer structures are those shown below:

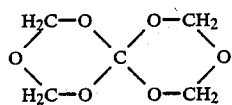

1,5,7,11-tetraoxaspiro
[5.5] undecane

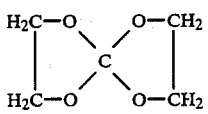

1,4,6,9-tetraoxaspiro
[4.4] nonane

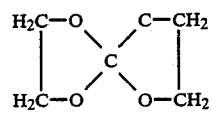

1,4,6-trioxaspiro
[4.4] nonane

These bicyclic oxa-spiro monomers polymerize through a ring opening mechanism in the presence of cationic initiators such as boron trifluorde etherate ($BF_3.OEt_2$).

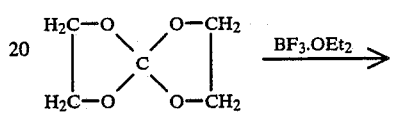

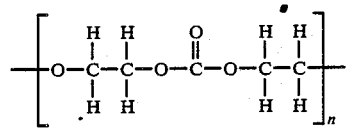

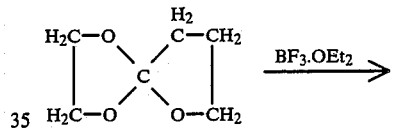

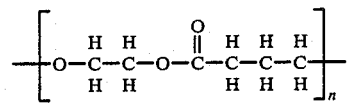

The predominant change which produces expansion is the breaking of two covalent bonds of the monomer for every new covalent bond formed. Several oxa-spiro monomers have been identified that exhibit between 0 and 17% expansion during polymerization. See Bailey, et al., supra. Some of these materials have been evaluated as comonomers with epoxy resins for controlling shrinkage and voids in insulation materials used in electrical equipment.

There are various organo-phosphorus monomers which undergo cationic ring-opening polymerization. For example, phospholanes and deoxophostones (5-membered ring monomers), phosphorinanes (6-membered monomers) and phosphocane (8-membered ring) all undergo cationic ring opening polymerization. See Kobayashi, et al., "Cationic Ring-Opening Polymerization of 2-Phenyl-1,3,2-dioxaphosphepane, a Seven Membered Cyclic Phosphonite, 19 Macromolecules 466-469 (1986). Cyclic phosphonites will polymerize to produce polyphosphinates as follows:

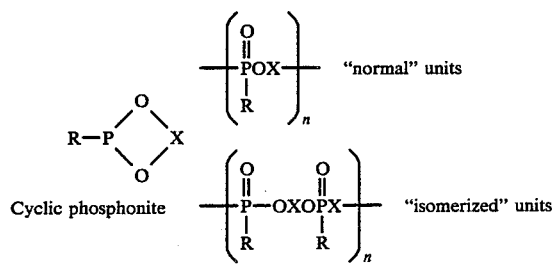

Cyclic phosphonite    "normal" units    "isomerized" units

X=(CH₂)₂, (CH₂)₃, (CH₂)₂O(CH₂)₂
R=Ph

Polymerization of deoxophostone produces poly(phosphine oxide)

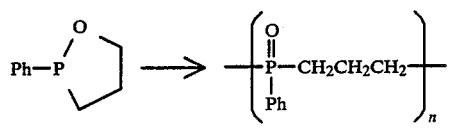

and the polymerization of 2-phenyl - 1,3,2-dioxaphosphepane (7-membered ring) produces polyphosphinates as follows:

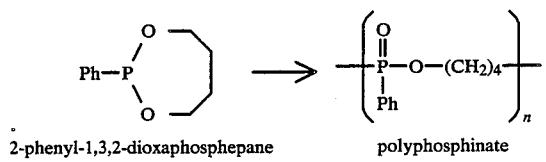

2-phenyl-1,3,2-dioxaphosphepane    polyphosphinate

The stereochemistry of these monomers is such that during polymerization significant volume expansion occurs as the cyclic ring opens up. This "uncoiling" effect during polymerization has been observed with certain cyclic keto-dilactones. See S. Klaus and W. S. Knowles, 10 J. App. Poly. Sci. 887 (1966).

Although the oxa-spiro and organo-phosphorus materials discussed above do exhibit zero shrinkage and even expansion upon polymerization, they exhibit less than desirable properties for certain applications. For example, these polymers exhibit low thermal stability at temperatures above about 120° C., and thus have only limited use in high voltage insulation applications.

Another drawback with the oxa-spiro compounds is that they tend to exhibit undesirable electrical properties, such as allowing high electrical losses stemming from having dielectric constants and dissipation factors which are too high for high voltage insulation applications.

Yet another problem associated with these oxa-spiro compounds is their tendency to burn rapidly, which is of great significance for polymers used in high voltage, high temperature situations.

Still further problems exhibited by these polymers are the fact that they exhibit less than desirable mechanical properties, including low tensile (modulus and strength) properties. Additionally, these polymers are frequently slow-curing, requiring very strong acid catalysts to cure.

Attempts to solve these problems by blending these polymers with other materials such as epoxies have improved some properties moderately, but have not resulted in any improvement in flame retardant and electrical properties.

Accordingly, it would be desirable to develop a high temperature polymer exhibiting zero shrinkage, and solving some or all of the above problems, such as the need for flame retardance.

SUMMARY OF THE INVENTION

The present invention comprises a method of producing high temperature organo-phosphorus polymers, as well as the polymers themselves. As used herein, the term "high temperature" means temperatures frequently encountered when operating in the high voltage range, typically 100°-200° C. for generators. Also as used herein, the term "high voltage" means up to 30 kV, typically 15 to 25 kV.

According to a preferred method of practicing the invention, an organo-phosphorus cyclic monomer is prepared, for example, phospholanes, deoxophostones, phosphorinanes and phosphocanes, and the ring of the cyclic monomer is opened using an acid catalyst. The opened monomer is then polymerized yielding an organo-phosphorus polymer exhibiting zero shrinkage and even expansion.

Because of the phosphorus content of the monomer, the resulting polymer should exhibit flame retardance, if not self extinguishing properties. Additionally, the polymers of the present invention will exhibit improved thermal stability relative to oxa-spiro and compounds previously known.

Additionally, the polymers of the present invention are likely coreactive with epoxy/oxa-spiro resins, and thus could be used to upgrade the properties of these materials. Polymers produced according to the present invention can find application in power equipment insulation, structural composites, adhesives and printed wiring boards.

Other details, objects and advantages of the invention will become apparent as the following description of the presently preferred embodiments and presently preferred methods of practicing the invention proceeds.

DETAILED DESCRIPTION OF THE INVENTION

According to a preferred embodiment of the present invention, an organo-phosphorus cyclic monomer is prepared, and the ring of the monomer is opened using an acid catalyst. The opened monomer is then polymerized to produce a polymer of the following structure:

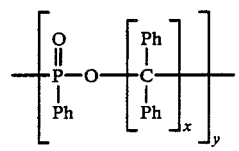

In a preferred embodiment of the invention, x=1-20 and preferably 8-10 and y is at least 10, and preferably at least 50.

This type of polymer structure can be derived from an organo-phosphorus monomer such as:

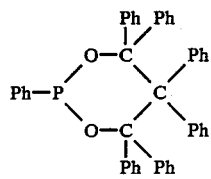 (1)

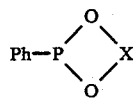 (2)

where X = 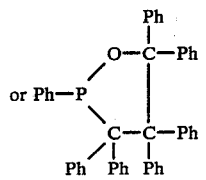

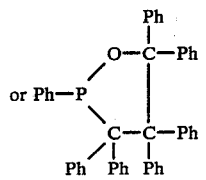 (3)

The phenyl groups of these organo-phosphorus monomers are resistant to oxidative attack and enhance the thermal stability of these organo-phosphorus polymers relative to oxa-spiro polymers and those containing aliphatic hydrocarbon groups.

Instead of phenyl groups, multicyclic aromatic groups such as naphthalene, anthracene and others could be used. Additionally, the phenyl groups may be replaced by alkylaryl groups, including for example $C_6H_5CH_2$, $(C_6H_5)_2CH$, $(C_6H_5)_3C$, $C_6H_5C(CH_3)_2$, $(C_6H_5)_2CCH_3$, $(C_6H_5)CHCH_3$, toluene, xylene, and mesitylene groups. Additionally, ethyl benzene, diethyl benzene and triethyl benzene could be used. Some of these groups are depicted below, with "a" marking the point of attachment of the group to the phosphorus atom in the polymer of the present invention.

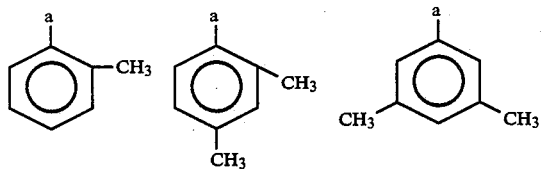

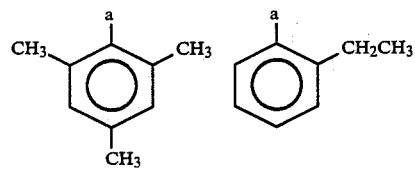

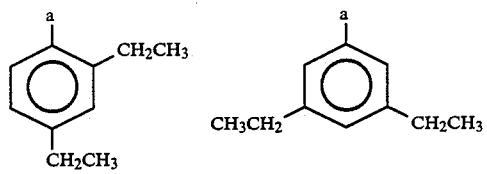

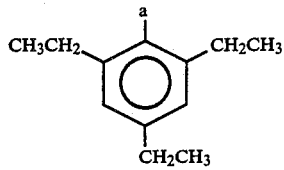

The phosphorus of the organo-phosphorous polymers of the present invention has the effect, due to its relatively large size, of pushing the polymer chains apart. This effect, in combination with O—H bonding and van der Waals forces between chains, produces a net volumetric expansion effect relative to the tightly bound cyclic monomers. That is to say, intramolecular forces predominate when the ring is closed, while intermolecular forces predominate in the polymerized form. As used herein, "intramolecular forces" refers to forces that operate within the structure of the same molecule, and "intermolecular forces" refers to forces between different or separate molecules. Indeed, it is believed that the structure of the polymers of the present invention will behave, due to the phenol groups, like a liquid crystal polymer, wherein self-alignment of polymer chains relative to one another produces improved mechanical and electrical properties.

It is expected that species other than phosphorus such as Bismuth, Arsenic, Silicon, and Nitrogen could exhibit similar expansion effects.

Additionally, the phosphorus permits flame-retardant, if not self-extinguishing, properties to be imputed directly to the polymer chain through chemical bonding, and as such, the flame retardant will not leach out of the polymer, a typical problem associated with flame retardant-impregnated polymers, wherein no chemical bonding is present.

Examples of methods for preparing preferred cyclic organo-phosphorus monomers and organo-phosphorus polymers according to the present invention follow.

A. Synthese of 2-Phenyl-1, 3, 2-Dioxa Tetraphenyl-Phosphepane, 2-Phenyl-1, 3, 2-Dioxaoctaphenyl-Phosphepane and 2-Phenyl-1, 3, 2-Dioxahezaphenyl-Phosphorinane

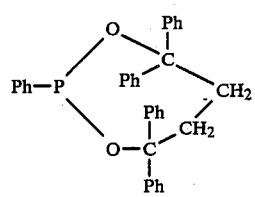 Monomer I

2-Phenyl-1,3,2-Dioxatetraphenyl-Phosphepane

Synthesis of Monomer I

To a cooled mixture of 1,1,4,4, Tetraphenyl-1,4-Butanediol (72.5g., 0.184 mol) in 200 ml of benzene and triethylamine (52.0 ml, 0.184 mol) was added a benzene solution of dichlorophenylphosphine (25.0 ml, 0.184 mol) dropwise at about 5° C. under nitrogen for 2 hours. The reaction mixture was then stirred at 60° C. for 30 hours. The resulting ammonium salt was removed by filtration. The monomer product was subsequently purified by vacuum distillation.

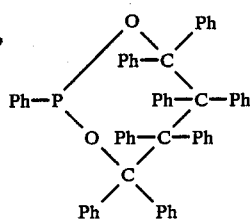

2-Phenyl-1,3,2-Dioxa Octaphenyl-Phosphepane

Synthesis of Monomer II

To a cooled mixture of Octaphenyl-1,4-Butanediol (128 g., 0.184 mol) in 200 ml of benzene and triethylamine (52.0 ml, 0.184 mol) was added a benzene solution of dichlorophenylphosphine (25.0 ml, 0.184 mol) dropwise at about 5° C. under nitrogen for 2 hours. The reaction mixture was then stirred at 60° C. for 30 hours. The resulting ammonium salt was removed by filtration. The monomer product was subsequently purified by vacuum distillation.

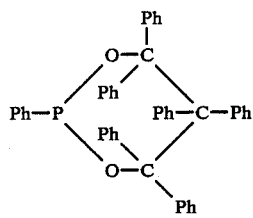

2-Phenyl-1,3,2-Dioxahexaphenyl Phosphorinane

Synthesis of Monomer III

To a cooled mixture of Hexaphenyl-1-1,3-Propanediol (98 g, 0.184 mol) in 200 mL of benzene and triethylamine (52.0 ml, 0.184 mol) was added a benzene solution of dichlorophenylphosphine (25.0 ml, 0.184 mol) dropwise at about 5° C. under nitrogen for 2 hours. The reaction mixture was then stirred at 60° C. for 30 hours. The resulting ammonium salt was removed by filtration. The monomer product was then purified by vacuum distillation.

B. Polymerization Procedures

A typical polymerization process according to a preferred method of practicing the present invention is as follows:

In a glass tube, 9.28 mmol of Monomer I, II or III and 0.16 mmol of Methyl Iodide were placed in 5 ml of dry benzonitrile under nitrogen. The tube was sealed and kept at 120° C. for 22 hours. The mixture was then poured into an excess of dry diethyl ether. The supernatant layer was decanted, and the precipitated waxy polymer in the bottom of the flask was washed several times with dry diethyl ether and then dried under vacuum.

Alternatively the polymerization was carried out in CHCl$_3$ solution with methyl iodide as catalyst under a N$_2$ atmosphere at ~80° C. in a sealed tube.

Other Lewis Acid catalysts such as CF$_3$SO$_3$H, BF$_3$, BCl$_3$PF$_5$, SbF$_5$ and SbCl$_5$ are also suitable for polymerization.

Some of these organo-phosphorus compounds e.g., the poly (phosphine oxides) may be coreactive with epoxy and oxa-spiro compounds, thereby providing a synthetic approach to upgrading the thermal characteristics of epoxy oxa-spiro copolymers without any deleterious effect on the expansion characteristics of these materials. See U.K. Pat. No. 1,355,932. Another added advantage of incorporating organo-phosphorus compounds into these structures would be to impart effective flame resistance characteristics, which may be extremely beneficial in some applications of these materials (e.g. composite structures). Preferably, these copolymerization reactions take place using from 10–90% organo-phosphorus polymer.

The following are examples of copolymerization reactions between these organophosphenes monomers and bisphenol (A) and cycloaliphatic epoxies.

EXAMPLE I

A 1:1 mole ratio mixture of Monomer I and DER 332 (a bisphenol 'A' epoxy resin available from the Dow Chemical Company) was polymerized as described above, using Boron Trifluoride: monomethylamine (BF$_3$:MEA) as catalyst. After several hours at 120° C. an intractable white polymer product was obtained.

EXAMPLE II

A 1:1 mole ratio mixture of Monomer II and a bicyclic oxa-spiro monomer compound (1,5,7,11-tetraoxaspiro (5.5) undecane) was polymerized as described previously using BF$_3$:MEA as catalyst. After several hours at 120° C. an intractable white polymer product was formed.

The applications which are contemplated for these high temperature expanding resins are:

1. void-free high voltage insulation materials for motors, generators and transformers.
2. Improved, flame-retardant matrix resins for structural composites.
3. High temperature adhesives and coatings.
4. High temperature, flame-retardant resins for laminated printed wiring boards.
5. For use in winding tape such as that described in U.S. Pat. No. 3,998,983.
6. As a replacement for mica/resin laminates used to cover generator coils.

I claim:

1. A method of producing high temperature organo-phosphorus polymers of the structure

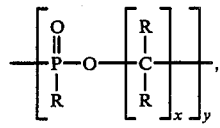

wherein R is selected from the group comprising phenyl, benzyl, naphthalene, anthracene or arylalkyl groups, wherein x=1–12 and y is at least 10, said method comprising the steps of:
   a. preparing an organo-phosphorous cyclic monomer;
   b. opening said cyclic monomer with use of an acid catalyst;
   c. curing said monomer to form said organo-phosphorus polymer, said polymer comprised of multiple monomeric units of said monomer, and said polymer exhibiting zero shrinkage.

2. The method of claim 1 wherein said curing of said organo-phosphorus cyclic monomer is accomplished with an epoxy resin to form a co-polymer of said epoxy resin and said organo-phosphorus cyclic monomer.

3. The method of claim 2 wherein said organo-phosphorus cyclic monomer comprises from 10–90% by weight of said co-polymer.

4. The method of claim 3 wherein said organo-phosphorus cyclic monomer comprises 50% of said co-polymer.

5. The method of claim 1 wherein said organo-phosphorus cyclic monomer is selected from the group 2-Phenyl-1,3,2-Dioxa Tetraphenyl-Phosphepane, 2-Phenyl-1,3,2-Dioxaoctaphenyl-Phosphepane and 2-Phenyl-1,3,2-Dioxahexaphenyl Phosphorinane.

6. The method of claim 1 wherein said curing is accomplished in the presence of a Lewis Acid catalyst.

7. The method of claim 6 wherein said Lewis Acid catalyst is selected from the group methyl iodide, $CF_3SO_3H, BF_3, PF_5$ and $SbCl_5$.

8. The method of claim 2 wherein said epoxy resin is a bisphenol (A) or cycloaliphatic epoxy resin.

9. An organo-phosphorous polymer of the structure:

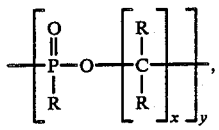

wherein R is selected from the group comprising phenyl, benzyl, naphthalene, anthracene or arylalkyl groups, wherein $x = 1-12$ and y is at least 10.

10. The polymer of claim 9 wherein said polymer exhibits zero shrinkage.

11. The polymer of claim 9 wherein said polymer exhibits expansion.

12. The polymer of claim 9 wherein said polymer exhibits high temperature stability.

13. The polymer of claim 9 wherein said polymer exhibits flame retardant properties.

14. High voltage, high temperature electrical insulation fabricated from the polymer of claim 9.

15. The polymer of claim 9 wherein R is selected from the group $C_6H_5CH_2$, $(C_6H_5)_2CH$, $(C_6H_5)_3C$, $C_6H_5C(CH_3)_2$, $(C_6H_5)_2CCH_3$, $(C_6H_5)CHCH_3$, toluene, xylene, and mesitylene groups.

16. A method of producing high temperature organo-phosphorus polymers comprising the steps of:
   a. preparing an organo-phosphorus cyclic monomer;
   b. opening said cyclic monomer with use of an acid catalyst;
   c. curing said opened cyclic monomer in the presence of an epoxy resin to form a co-polymer of said opened cyclic monomer and said epoxy resin, said epoxy resin being a bisphenol (A) or cycloalighatic epoxy resin.

* * * * *